United States Patent
Raths et al.

(10) Patent No.: US 6,300,508 B1
(45) Date of Patent: Oct. 9, 2001

(54) THICKENED AQUEOUS SURFACTANT SOLUTIONS

(75) Inventors: Hans-Christian Raths, Monheim (DE); Norman Milstein, Montgomery, OH (US); Werner Seipel, Hilden (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/109,341

(22) Filed: Jun. 30, 1998

Related U.S. Application Data

(60) Provisional application No. 60/054,370, filed on Jul. 30, 1997.

(51) Int. Cl.$^7$ .................................................. C07C 51/00
(52) U.S. Cl. ............................. 554/149; 424/45; 516/38; 516/46; 516/51
(58) Field of Search .............................. 424/45; 554/149; 516/38, 46, 51

(56) References Cited

U.S. PATENT DOCUMENTS

| | | | |
|---|---|---|---|
| 3,884,946 | 5/1975 | Sung et al. | 260/400 |
| 4,722,811 | 2/1988 | Godwin | 260/410.6 |
| 4,992,263 | 2/1991 | Tesmann et al. | 424/63 |
| 5,034,159 | 7/1991 | Tesmann et al. | 252/551 |
| 5,679,324 | * 10/1997 | Lisboa et al. | 424/45 |
| 5,888,478 | * 3/1999 | Maurin | 424/45 |

FOREIGN PATENT DOCUMENTS

| | | |
|---|---|---|
| 3730179 | 3/1989 | (DE) . |
| 3817415 | 11/1989 | (DE) . |

OTHER PUBLICATIONS

Chem. Abstrs. 107:178706, 1987.*

* cited by examiner

*Primary Examiner*—Deborah D. Carr
(74) *Attorney, Agent, or Firm*—John F. Drach; Steven J. Trzaska

(57) ABSTRACT

Fatty acid esters of alkylene glycols corresponding to the formula $R^1COO(AlkO)_nH$ are thickeners for aqueous surfactant solutions, particularly for personal care products.

20 Claims, No Drawings

THICKENED AQUEOUS SURFACTANT SOLUTIONS

CROSS REFERENCE TO RELATED APPLICATIONS

This application claims priority from U.S. provisional application Ser. No. 60/054,370, filed Jul. 30, 1997, the disclosure of which is incorporated herein by reference.

FIELD OF THE INVENTION

This invention relates to aqueous surfactant solutions containing fatty acid ester of alkylene glycols as thickeners, to the use of fatty acid alkylene glycols as thickeners in aqueous surfactant solutions and to processes for the production of fatty acid esters of propylene glycols and for the production of fatty acid esters of ethylene propylene glycols.

BACKGROUND OF THE INVENTION

Aqueous surfactant solutions, particularly those used in the field of personal care as hair shampoos, foam baths, shower baths, hand washing pastes and the like, mostly contain anionic surfactants, for example alkyl ether sulfates. In order to stabilize these clear or disperse systems and to make them easier for the user to handle, thickeners are normally added to the surfactant solutions. Various inorganic and organic compounds used to increase the viscosity of anionic surfactant solutions are known to the expert. Water-soluble electrolyte salts, typically sodium chloride, are generally used as inorganic thickeners. Examples of organic thickeners are fatty acid alkanolamides, polyethylene glycol difatty acid esters and a number of water-soluble polymers. In most cases, the required viscosity of the surfactant solution can be adjusted with inorganic electrolyte salts alone, but only by using large quantities. Accordingly, organic thickeners are generally used in addition to the inorganic salts although, in some cases, they are attended by a number of disadvantages. Thus, surfactant solutions thickened with polyethylene glycol fatty acid diesters often show inadequate viscosity stability in storage while water-soluble polymers show unwanted slimy flow behavior with a tendency to become stringy in the thickened surfactant solutions.

Accordingly, it is proposed in German patent applications DE-A-37 30 179 and DE-A-38 17 415 to use addition products of ethylene oxide and/or propylene oxide, optionally with a narrow homolog distribution, with saturated and/or unsaturated fatty alcohols for thickening surfactant solutions. These products are not attended by the disadvantages mentioned above. However, there is a need for further organic thickeners with an increased thickening effect which make it possible in particular to use low contents of organic and inorganic thickeners for a given viscosity to be adjusted in the surfactant solution.

It has now surprisingly been found that this problem can be solved by using fatty acid esters of alkylene glycols as thickeners.

DESCRIPTION OF THE INVENTION

Accordingly, the present invention relates to thickened aqueous surfactant solutions which are characterized in that they contain as organic thickeners fatty acid esters of alkylene glycols corresponding to formula (I):

$$R^1COO(AlkO)_nH \qquad (I)$$

in which $R^1CO$ is a linear or branched, aliphatic, saturated and/or unsaturated acyl group containing 6 to 22 carbon atoms, Alk stands for $—CH_2CH_2—$, $—CH_2CH_2CH_2—$ and/or $—CH_2CH(CH_3)—$ and n is a number of 0.5 to 5.

In the context of the present invention, the expression "thickened" means that the thickened surfactant solutions have a demonstrably higher viscosity than the unthickened surfactant solutions, as determined by physicochemical methods, more particularly with a Brookfield viscometer. In addition, the terms "thickener" and "thickening agent" are used synonymously.

The fatty acid esters of alkylene glycols are products of the addition of ethylene oxide and/or propylene oxide to fatty acids with the formula $R^1COOH$, where $R^1CO$ is as defined above. Typical examples are caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example, cocofatty acid, palm oil fatty acid, palm kernel oil fatty acid or tallow fatty acid, are preferred.

Ethoxylated, propoxylated or ethoxylated and propoxylated fatty acids with a degree of alkoxylation n of 1 to 2 are particularly preferred. The fatty acids in question may be exclusively propoxylated fatty acids, exclusively ethoxylated fatty acids or both ethoxylated and propoxylated fatty acids, the ethoxylated/propoxylated fatty acids being both random and block compounds.

The ethoxylated and/or propoxylated fatty acids, which are also known as fatty acid esters of alkylene glycols, are known compounds. They may be prepared, for example, by reaction of carboxylic acids with alkylene oxides in the presence of amines as catalysts as described in U.S. Pat. No. 3,884,946, the entire contents of which are incorporated herein by reference. Better yields can be obtained for low-ethoxylated fatty acids by the process described in copending patent application Ser. No. 08/767,123, filed Dec. 9, 1996, the entire contents of which are incorporated herein by reference. In this process, the ethoxylation is carried out in the presence of alkanolamines as catalysts and gives distinctly higher yields. In the development of the present invention, it was found that the propoxylation or propoxylation/ethoxylation of the fatty acids can also be carried out in the presence of alkanolamines. Accordingly, the present invention also relates to a process for the production of fatty acid esters of propylene glycol corresponding to formula (II):

$$R^1COO(PO)_nH \qquad (II)$$

in which $R^1CO$ has the same meaning as defined for formula (I), PO stands for $—CH_2CH_2CH_2O—$ and/or $—CH_2CH(CH_3)O—$ and n is a number of 0.5 to 5, and fatty acid esters of ethylene propylene glycols corresponding to formula (III):

$$R^1COO(EO)_x(PO)_y(EO)_zH \qquad (III)$$

in which $R^1CO$ has the same meaning as defined for formula (I), EO stands for $—CH_2CH_2O—$, PO stands for —CH$_2$CH$_2$CH$_2$O— and/or —CH$_2$CH(CH$_3$)O— and x=0–5, y=0.1–5 and z=0–5, the sum of x and z being greater than 0 and the sum of x, y and z being in the range from 0.5 to 5, by propoxylation or propoxylation/ethoxylation of fatty acids, characterized in that the propoxylation or ethoxylation/propoxylation reaction is carried out in the presence of alkanolamines as catalysts.

Typical examples of alkanolamines suitable for use as basic catalysts are monoethanolamine, diethanolamine and preferably triethanolamine. The alkanolamines are normally used in quantities of 0.1 to 5% by weight and preferably in quantities of 0.5 to 3.0% by weight, based on the fatty acids.

The propoxylation and/or ethoxylation/propoxylation reaction may be carried out in known manner. The fatty acid and the catalyst are normally introduced into a stirred autoclave which is freed from traces of water before the reaction by alternate evacuation and purging with nitrogen. The fatty acid is then reacted with the propylene oxide or with the ethylene oxide/propylene oxide mixture in a molar ratio of 1:0.5 to 1:5 which may be introduced into the autoclave in portions through a siphon after heating. The fatty acids are preferably reacted with 1 to 2 moles of propylene oxide or with 1 to 2 moles of the mixture of ethylene and propylene oxide. The reaction may be carried out at temperatures of 80 to 180° C. and preferably 100 to 120° C. under autogenous pressures of 1 to 5 bar and preferably 2 to 3 bar. After the reaction, it is advisable to stir the reaction mixture for a certain time (15–90 mins.) at the reaction temperature in order to complete the reaction. The autoclave is then cooled, vented and, if desired, acids, for example, lactic acid or phosphoric acid, are added to the product to neutralize the basic catalyst.

The fatty acid esters of alkylene glycol of the type described above are normally present in the thickened aqueous surfactant solutions according to the invention in quantities of 0.2 to 5% by weight, based on surfactant solution. The surfactant solutions additionally contain 3 to 30% by weight of surfactants and 0 to 10% by weight of water-soluble inorganic and/or organic electrolyte salts. The balance to 100% by weight of the surfactant solution is water.

The surfactants may be ionic surfactants, nonionic surfactants or mixtures of ionic and nonionic surfactants.

Anionic, zwitterionic and cationic surfactants may be present as the ionic surfactants. Suitable ionic surfactants are distinguished by a lipophilic, preferably linear alkyl or alkylene group containing 8 to 18 carbon atoms and an ionic group dissociating in water preferably attached terminally thereto. The anionic group may be, for example, a sulfate, sulfonate, phosphate or carboxylate group. The cationic group may be, for example, a quaternary ammonium group. The ionic surfactants are preferably anionic surfactants. Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (more particularly wheat-based vegetable products) and alkyl (ether) phosphates. If the anionic surfactants contain polyglycol ether chains, they may have a conventional homolog distribution although they preferably have a narrow homolog distribution. Preferred anionic surfactants are alkyl sulfates, fatty alcohol ether sulfates, alkane sulfonates and/or ether carboxylic acids, fatty alcohol ether sulfates being particularly preferred.

Instead of the anionic surfactants, cationic surfactants may also be present. Typical examples of cationic surfactants are quaternary ammonium compounds and esterquats, more particularly quaternized fatty acid trialkanolamine ester salts.

Zwitterionic surfactants may also be present either on their own or in admixture with another ionic surfactant providing there are no troublesome interactions. Typical examples of amphoteric or zwitterionic surfactants are alkyl betaines, alkyl amidobetaines, aminopropionates, aminoglycinates, imidazolinium betaines and sulfobetaines. Within this group, alkyl betaines and alkyl amidobetaines are particularly preferred. Alkyl betaines are known surfactants which are mainly produced by carboxyalkylation, preferably carboxymethylation of aminic compounds. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, C$_{12/14}$ cocoalkyl dimethyl amine, myristyl dimethyl amine, cetyl dimethyl amine, stearyl dimethyl amine, stearyl ethyl methyl amine, oleyl dimethyl amine, C$_{16/18}$ tallow alkyl dimethyl amine and technical mixtures thereof.

Alkyl amidobetaines which represent carboxyalkylation products of amidoamines are also suitable. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethyl amine, N,N-dimethylaminoproply amine, N,N-diethylaminoethyl amine and N,N-diethylaminoproply amine which are condensed with sodium chloroacetate. The condensation product of C$_{8/18}$ cocofatty acid-N,N-dimethylaminopropyl amide with sodium chloroacetate is preferably used.

In addition, nonionic surfactants may be present either on their own or in admixture with the ionic surfactants. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, alk(en)yl oligoglucosides, fatty acid-N-alkyl glucamides, protein hydrolyzates (more particularly soya-based vegetable products), polyol fatty acid esters, sugar esters, sorbitan esters and polysorbates. If the nonionic surfactants contain polyglycol ether chains, they may have a conventional homolog distribution although they preferably have a narrow homolog distribution. Particularly preferred nonionic surfactants are alkyl and/or alkenyl oligoglycosides.

Alkyl and alkenyl oligoglycosides are known nonionic surfactants corresponding to formula (IV):

in which R$^2$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry.

The alkyl and/or alkenyl oligoglycosides may be derived from aldoses or ketoses containing 5 or 6 carbon atoms, preferably from glucose. Accordingly, the preferred alkyl and/or alkenyl oligoglycosides are alkyl and/or alkenyl oligoglucosides.

The index p in general formula (IV) indicates the degree of oligomerization (DP degree), i.e., the distribution of monoglycosides and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides with an average degree of oligomerization p of 1.1 to 3.0 are preferably used. From the performance point of view, alkyl and/or alkenyl oligoglycosides with a degree of oligomerization below 1.7 and, more particularly, between 1.2 and 1.4 are preferably used.

The alkyl or alkenyl group $R^2$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides with a chain length of $C_8$ to $C_{10}$ (DP=1.1 to 3), which are obtained as first runnings in the separation of technical $C_{8/18}$ cocofatty alcohol by distillation and which may contain less than 6% by weight of $C_{12}$ alcohol as an impurity, and alkyl oligoglucosides based on technical $C_{9/11}$ oxoalcohols (DP=1 to 3) are preferred.

In addition, the alkyl or alkenyl group $R^2$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and the technical mixtures thereof obtained as described above. Alkyl oligoglucosides based on hydrogenated $C_{12/14}$ cocoalcohol with a DP of 1.1 to 3 are preferred.

In a particularly preferred embodiment of the invention, the surfactants to be thickened are mixtures of anionic surfactants, preferably alkyl ether sulfates, and zwitterionic surfactants, preferably alkyl amidobetaines, and nonionic surfactants, preferably alkyl (alkylene) oligoglucosides, the ratio by weight of the mixtures preferably being from 1:1:1 to 10:1:1.

Suitable inorganic electrolyte salts are any water-soluble alkali metal, ammonium and/or alkaline earth metal salts, such as the fluorides, chlorides, bromides, sulfates, phosphates and nitrates providing they are soluble in water at 20° C. in a quantity of at least 1% by weight. The chlorides or sulfates of an alkali metal, ammonium or magnesium are preferably used. Sodium chloride (common salt) and magnesium chloride are particularly preferred.

Suitable organic electrolyte salts are, in particular, any water-soluble alkali metal, ammonium and alkaline earth metal salts of mono-, di- and tricarboxylic acids. Carboxylic acids with a molecular weight of less than 200 g/mole are preferred.

In addition, the aqueous formulations according to the invention may contain other components which make them suitable for the particular application envisaged. For example, they may contain small amounts of fragrances, dyes, opacifiers and pearlescers, antimicrobial agents, preservatives, active skin-care substances, plant extracts, protein hydrolyzates, buffers, complexing agents and other known auxiliaries and additives typically present in shampoos, bath additives, shower baths, liquid skincleansing preparations, liquid hair shampoos and in liquid laundry and dishwashing detergents and liquid domestic cleaners based on ionic surfactants.

Increasing the viscosity of aqueous solutions of the described type with a comparatively small amount of organic thickeners and inorganic thickening electrolyte salts is of particular interest from the applicational point of view. By using the described fatty acid esters of alkylene glycols, the thickening effect of the inorganic electrolyte salts is enhanced, above all synergistically, so that the quantity of inorganic electrolyte salts used can be reduced for the same viscosity.

Finally, the present invention also relates to the use of the fatty acid esters of alkylene glycols corresponding to formula (I) as organic thickeners for aqueous surfactant solutions.

EXAMPLES

The following examples are meant to illustrate but not to limit the invention.

Example 1

In a 1 liter stirred autoclave, 6 g of triethanolamine (corresponding to 3% by weight, based on lauric acid) were added to 200 g (1 mole) of technical lauric acid. The autoclave was alternately evacuated and purged with nitrogen a total of three times to remove traces of water which could lead to the formation of polyethylene glycol. After the reaction mixture had been purged with nitrogen for the last time, the autoclave was closed, heated to 100° C. and charged in portions with 59 g (1 mole) of propylene oxide at a maximum pressure of 5 bar. On completion of the reaction, which was reflected in the fact that the pressure fell back to a value of 1.2 bar and then remained constant, the reaction mixture was stirred for 30 minutes and then cooled and vented. The basic catalyst was neutralized by addition of a corresponding quantity of lactic acid. The characteristic data of the lauric acid+1 PO adduct are (quantities in % by weight):
Free fatty acid: 3.6
Fatty acid+1 PO: 94.0
Fatty acid+2 PO: 1.1
Diester: 1.3

Example 2

A lauric acid+1 EO adduct was prepared as in Example 1 using 44 g of ethylene oxide. The characteristic data of the lauric acid+1 EO adduct are (quantities in % by weight):
Free fatty acid: 2.2
Fatty acid+1 EO: 97.0
Diester: 0.8

Application Example 3

(Thickenability)

2% by weight of the lauric acid propoxylate produced in accordance with Example 1 was added with stirring to a 10% by weight aqueous solution of a $C_{12/14}$ fatty alcohol ether sulfate ethoxylated with 2 moles of ethylene oxide (as sodium salt) which was then thickened by addition of 1.25% by weight of sodium chloride.

A viscosity (Brookfield, spindle 1, room temperature, 20 r.p.m.) of 8140 mPas was established.

For comparison, 3% by weight of a nonionic thickener ($C_{12/14}$ fatty alcohol ethoxylated with 2.5 moles ethylene oxide, narrow homolog distribution) was added to the same fatty alcohol sulfate solution as in the Application Example. The solution was then thickened by addition of 1.5% by weight of sodium chloride. A viscosity of 8500 mPas was established.

The Comparison Example shows that smaller quantities of the organic thickener according to the invention (lauric acid+1 PO) and thickening sodium chloride are used for substantially the same viscosity to be adjusted.

Application Example 4

(Thickenability)
a) 2% by weight of the lauric acid+1 PO adduct produced in accordance with Example 1,
b) 2% by weight of the lauric acid+1 EO adduct produced in accordance with Example 2 and, for comparison,
c) 2% by weight of a nonionic thickener ($C_{12/14}$ fatty alcohol ethoxylated with 2.5 moles of ethylene oxide, narrow homolog distribution)

were added to aqueous solutions (12% WAS) of 5.7% by weight of an aqueous solution of a $C_{12/14}$ fatty alcohol ether sulfate ethoxylated with 2 moles of ethylene oxide; Na salt (28% active substance) and 6.0% by weight of an aqueous solution of a cocoamidopropyl betaine (40%, contains 5.5 to 7% by weight of sodium chloride); DEHYTON PK45® and 4.8% by weight of a $C_{8-14}$ alkyl glucoside with a DP of 1.4 (52% active substance).

The following viscosities (Brookfield, spindle 4, 10 r.p.m., 23° C.) were established:
a) 6800 mPas
b) 5200 mPas
c) 2200 mPas.

It can be seen that the thickeners according to the invention are very much better thickeners than commercial nonionic thickeners.

What is claimed is:

1. A process for the production of a fatty acid ester of an ethylene-propylene glycol of the formula (III):

$$R^1COO(EO)_x(PO)_y(EO)_zH \quad (III)$$

wherein $R^1CO$ is a linear aliphatic, saturated or unsaturated acyl group, or a combination thereof, having from about 6 to about 22 carbon atoms, EO is —$CH_2CH_2$—, PO is —$CH_2CH(CH_3)O$— or —$CH_2CH_2CH_2O$— or a combination thereof, and x=0 to about 5, y=about 0.1 to about 5 and z=0 to about 5, such that the sum of x and z is greater than 0 and the sum of x, y and z is in the range from about 0.5 to about 5, comprising reacting a fatty acid having from about 6 to about 22 carbon atoms with an alkylene oxide selected from the group consisting of propylene oxide, ethylene oxide or a combination thereof, in the presence of an alkanolamine.

2. The process of claim 1 wherein the fatty acid is reacted with from about 1 to about 2 moles of a mixture of ethylene oxide and propylene oxide per mole of fatty acid.

3. The process of claim 1 wherein the alkanolamine is from about 0.1 to about 5% by weight based on the weight of the fatty acids.

4. The process of claim 1 wherein the alkanolamine is selected from the group consisting of monoethanolamine, diethanolamine, triethanolamine or a combination thereof.

5. The process of claim 1 wherein the amount of alkanolamine is from about 0.1 to about 5% by weight based on the fatty acid.

6. The process of claim 1 wherein said process is carried out at a temperature of from about 80° to about 180° C.

7. The process of claim 1 wherein said process is carried out at a pressure of from about 1 bar to about 5 bar.

8. A product of the process of claim 1.

9. An aqueous composition comprising an ionic surfactant and from 0.5 to 3% by weight of a fatty acid ester of an alkylene glycol thickener of the formula (I):

$$R^1COO(AlkO)_nH \quad (I)$$

wherein $R^1CO$ is a linear or branched, aliphatic, saturated or unsaturated acyl group or a combination thereof, having from about 6 to about 22 carbon atoms, Alk is —$CH_2$—$CH_2$— or —$CH_2$—$CH_2$—$CH_2$— or $$-CH_2-\underset{CH_3}{CH}-$$

and n is from about 0.5 to about 2.

10. The aqueous composition of claim 1 wherein the amount of the thickener is from about 0.2 to about 5% by weight based on the weight of the aqueous composition.

11. The aqueous composition of claim 1 wherein the composition further comprises a water-soluble electrolyte salt, wherein the amount of the ionic surfactant is from about 3% to about 30% by weight based on the weight of the aqueous composition and wherein the amount of the water soluble electrolyte salt is from 0% to about 10% by weight based on the weight of the aqueous composition.

12. The aqueous composition of claim 1 wherein the ionic surfactant is selected from the group consisting of alkyl sulfates, fatty alcohol ether sulfates, alkane sulfonates, ether carboxylic acids and mixtures thereof.

13. A process for thickening an aqueous surfactant solution comprising adding an effective amount of the fatty acid ester of an alkylene glycol of claim 1 to an aqueous solution comprised of a surfactant.

14. The aqueous composition of claim 1 further comprising an alkyl or alkenyl oligoglycoside or a combination thereof, of the formula (IV):

$$R^2O-[G]_p \quad (IV)$$

wherein $R^2$ is an alkyl or alkenyl group or a combination thereof, containing from about 4 to about 22 carbon atoms, G is a sugar unit having from about 5 or about 6 carbon atoms and p is a number from about 1 to about 10.

15. The aqueous composition of claim 14 wherein p is from about 1.1 to about 3.0.

16. An aqueous composition comprising a surfactant and a fatty acid ester of an alkylene glycol thickener of the formula (III):

$$R^1COO(EO)_x(PO)_y(EO)_zH \quad (III)$$

wherein $R^1CO$ is a linear or branched aliphatic, saturated or unsaturated acyl group or a combination thereof, having from about 6 to about 22 carbon atoms, EO is —$CH_2CH_2O$—, PO is —$CH_2CH(CH_3)O$— or —$CH_2CH_2CH_2O$— and x=0 to 5, y=0.1 to 5 and z=0 to 5, such that the sum of x and z is greater than 0 and the sum of x, y and z is in the range from about 0.5 to about 2.

17. The aqueous composition of claim 16 wherein the amount of the thickener is from about 0.2 to about 5% by weight based on the weight of the aqueous composition.

18. The aqueous composition of claim 16 further comprising an ionic surfactant, wherein the amount of the ionic surfactant is from about 3% to about 30% by weight based on the weight of the aqueous composition.

19. A process for thickening aqueous surfactant solutions comprising adding an effective amount of the fatty acid ester of an alkylene glycol of claim 16 to an aqueous solution comprised of a surfactant, wherein the effective amount of the fatty acid ester of an alkylene glycol is from about 0.2 to about 5% by weight based on the weight of the aqueous composition.

20. The process of claim 19 wherein the aqueous solution further comprises an ionic surfactant and a water-soluble electrolyte salt, wherein the amount of the ionic surfactant is from about 3% to about 30% by weight based on the weight of the aqueous composition and wherein the amount of the water soluble electrolyte salt is from 0% to about 10% by weight based on the weight of the aqueous composition.

* * * * *